United States Patent
Lei et al.

(10) Patent No.: US 10,569,301 B2
(45) Date of Patent: Feb. 25, 2020

(54) POWER SUPPLY FOR ELECTROMAGNETIC ACOUSTIC TRANSDUCER (EMAT) SENSORS

(71) Applicant: ULC Robotics, Inc., Hauppauge, NY (US)

(72) Inventors: Qin Lei, Chandler, AZ (US); Junjun Xin, Ronkonkoma, NY (US)

(73) Assignee: ULC Robotics, Inc., Hauppauge, NY (US)

( * ) Notice: Subject to any disclaimer, the term of this patent is extended or adjusted under 35 U.S.C. 154(b) by 242 days.

(21) Appl. No.: 15/631,029

(22) Filed: Jun. 23, 2017

(65) Prior Publication Data

US 2018/0369864 A1 Dec. 27, 2018

(51) Int. Cl.
| | |
|---|---|
| *B06B 1/04* | (2006.01) |
| *H02M 1/08* | (2006.01) |
| *G01N 29/24* | (2006.01) |
| *B64C 39/02* | (2006.01) |
| *G01N 29/22* | (2006.01) |
| *G01N 29/265* | (2006.01) |
| *H02M 3/335* | (2006.01) |
| *H02M 7/5387* | (2007.01) |
| *H02M 1/00* | (2006.01) |

(52) U.S. Cl.
CPC .............. *B06B 1/04* (2013.01); *B06B 1/045* (2013.01); *B64C 39/024* (2013.01); *G01N 29/225* (2013.01); *G01N 29/2412* (2013.01); *G01N 29/265* (2013.01); *H02M 1/08* (2013.01); *B64C 2201/042* (2013.01); *B64C 2201/12* (2013.01); *B64D 2221/00* (2013.01); *G01N 2291/0425* (2013.01); *G01N 2291/0426* (2013.01); *H02M 3/33592* (2013.01); *H02M 7/53871* (2013.01); *H02M 2001/007* (2013.01); *Y10S 901/01* (2013.01); *Y10S 901/46* (2013.01)

(58) Field of Classification Search
CPC ..... B06B 1/04; B06B 1/045; B64C 2201/042; B64C 2201/12; B64C 39/024; H02M 1/08; H02M 3/33592; H02M 7/53871; H02M 2001/007; B64D 2221/00; G01N 29/225; G01N 29/2412; G01N 29/265; G01N 2291/0425; G01N 2291/0426; Y10S 901/01; Y10S 901/46
USPC ............................................................ 73/643
See application file for complete search history.

(56) References Cited

U.S. PATENT DOCUMENTS

| | | | |
|---|---|---|---|
| 4,769,753 A | * | 9/1988 | Knudson ............... H02M 3/07 307/110 |
| 5,426,388 A | | 6/1995 | Flora et al. |
| 5,449,958 A | | 9/1995 | MacLauchlan et al. |

(Continued)

*Primary Examiner* — Natalie Huls
*Assistant Examiner* — Monica S Young
(74) *Attorney, Agent, or Firm* — Brooks Kushman P.C.

(57) ABSTRACT

An electromagnetic acoustic transducer (EMAT) system for inspecting a part includes an EMAT sensor and a power supply for supplying an output power to the EMAT sensor. The power supply includes a DC/DC converter to boost an input DC voltage into a boosted DC voltage, a DC/AC inverter having Silicon Carbide (SiC) Mosfet power switches to invert the boosted DC voltage into an AC square voltage, and an output filter to filter the AC square voltage into an AC sinusoidal voltage. The AC sinusoidal voltage is the output power from the power supply to the EMAT sensor.

17 Claims, 8 Drawing Sheets

(56) References Cited

U.S. PATENT DOCUMENTS

| | | | |
|---|---|---|---|
| 5,514,935 A * | 5/1996 | Oda | H05B 41/2886 315/308 |
| 5,721,379 A | 2/1998 | Palmer et al. | |
| 6,920,792 B2 | 7/2005 | Flora et al. | |
| 7,437,934 B2 | 10/2008 | Shoureshi | |
| 7,679,941 B2 * | 3/2010 | Raju | H02M 7/217 363/37 |
| 8,502,420 B1 * | 8/2013 | Mogilevski | H02M 3/33592 307/151 |
| 8,509,031 B2 | 8/2013 | Smith | |
| 9,201,045 B2 | 12/2015 | Jamoussi et al. | |
| 9,985,515 B1 * | 5/2018 | Nikitin | H02M 7/53875 |
| 2004/0227521 A1 * | 11/2004 | Higashihama | G01R 31/025 324/522 |
| 2007/0086222 A1 * | 4/2007 | Iida | H02J 7/022 363/37 |
| 2008/0316774 A1 * | 12/2008 | Ito | B60K 6/48 363/17 |
| 2009/0034300 A1 * | 2/2009 | Ito | H02M 1/4233 363/17 |
| 2009/0102443 A1 * | 4/2009 | Smith | B06B 1/0269 323/282 |
| 2009/0244947 A1 * | 10/2009 | Fornage | H02M 1/32 363/136 |
| 2010/0254221 A1 * | 10/2010 | Smith | B06B 1/0215 367/137 |
| 2011/0007537 A1 * | 1/2011 | Fornage | H02M 1/08 363/132 |
| 2013/0235630 A1 * | 9/2013 | Sadwick | H02M 3/335 363/74 |
| 2014/0369090 A1 * | 12/2014 | Ueki | H02M 1/15 363/41 |
| 2015/0256104 A1 * | 9/2015 | Fu | H02M 7/537 363/131 |
| 2015/0263644 A1 * | 9/2015 | Fu | H02M 7/487 363/95 |
| 2016/0268926 A1 * | 9/2016 | Becattini | H02M 7/53871 |
| 2016/0352229 A1 * | 12/2016 | Norimatsu | H02J 3/385 |
| 2017/0019095 A1 * | 1/2017 | Leong | H03K 17/167 |
| 2018/0034386 A1 * | 2/2018 | Okuda | H02M 3/155 |
| 2018/0205334 A1 * | 7/2018 | Dong | H02J 3/382 |
| 2018/0205335 A1 * | 7/2018 | Dong | H02K 11/33 |
| 2018/0234044 A1 * | 8/2018 | Yohanan | H02P 27/047 |
| 2019/0123662 A1 * | 4/2019 | Zhang | H02M 1/126 |
| 2019/0172683 A1 * | 6/2019 | Mavretic | H01J 37/32174 |
| 2019/0199193 A1 * | 6/2019 | Gloes | H02M 1/08 |
| 2019/0199194 A1 * | 6/2019 | Nikitin | H02M 1/08 |

* cited by examiner

POWER SUPPLY FOR ELECTROMAGNETIC ACOUSTIC TRANSDUCER (EMAT) SENSORS

TECHNICAL FIELD

The present invention relates to using electromagnetic acoustic transducer (EMAT) sensors for inspection of parts such as pipelines.

BACKGROUND

An electromagnetic acoustic transducer (EMAT) sensor is a sensor for ultrasonic inspection of a part to be inspected. The EMAT sensor generates an electromagnetic field which interacts with the part to generate an ultrasound in the part. The ultrasound travels through the part and reflects backwards to the EMAT sensor. The EMAT sensor detects wall thickness, wall loss, and defects such as cracks of the part based on the transmitted and received ultrasound.

EMAT sensors include EMAT bulk wave sensors and EMAT guided wave sensors. EMAT bulk wave sensors ("EMAT normal beam sensors") have a normal beam orientation as the beam is normal to the surface of the part being inspected. EMAT guided wave sensors have a beam that can travel in the circumferential or axial direction of the part being inspected.

A power supply (i.e., a pulser) supplies electrical power to an EMAT sensor. The EMAT sensor uses the power to generate the electromagnetic field which causes the ultrasound to be generated in the part being inspected. The power supply is physically connected to the EMAT sensor to provide the power to the EMAT sensor. The EMAT sensor may be attached, for example, to a robot that can physically access the part or to an unmanned aerial vehicle (UAV) that can fly over the part from a distance. Thus, the power supply is also attached, for example, to the robot or the UAV.

SUMMARY

A low distortion, high power density, pulse power supply for electromagnetic acoustic transducer (EMAT) sensors including EMAT normal beam sensors and/or EMAT guided wave sensors is provided.

In an embodiment, an EMAT system for inspecting a part is provided. The EMAT system includes an EMAT sensor and a power supply for supplying an output power to the EMAT sensor. The power supply includes a DC/DC converter to boost an input DC voltage into a boosted DC voltage, a DC/AC inverter having Silicon Carbide (SiC) Mosfet power switches to invert the boosted DC voltage into an AC square voltage, and an output filter to filter the AC square voltage into an AC sinusoidal voltage. The AC sinusoidal voltage is the output power from the power supply to the EMAT sensor. No transformer is used on the AC side to boost the voltage.

The power switches of the DC/AC inverter may be 1.2 kV SiC Mosfet power switches capable of switching at a switching frequency of at least up to 2.0 MHz or may be 1.7 kV SiC Mosfet power switches capable of switching at a switching frequency of at least up to 2.0 MHz when a higher output voltage is required.

In an embodiment, the EMAT sensor is an EMAT normal beam sensor. The DC/DC converter to boost the input DC voltage into the boosted DC voltage (500 V DC or higher). The DC/AC inverter to invert the boosted DC voltage into the AC square voltage (±600 V AC or higher) at a frequency between 1.5-2.0 MHz. The output filter to filter the AC square voltage into the AC sinusoidal voltage (±600 V AC or higher) at the frequency between 1.5-2.0 MHz. The AC sinusoidal voltage at the frequency between 1.5-2.0 MHz is the output power from the power supply to the EMAT normal beam sensor.

In an embodiment, the EMAT sensor is an EMAT guided wave sensor. The DC/DC converter to boost the input DC voltage into the boosted DC voltage (500 V DC or higher). The DC/AC inverter to invert the boosted DC voltage into the AC square voltage (±600 V AC or higher) at a frequency between 50-200 kHz. The output filter to filter the AC square voltage into the AC sinusoidal voltage (±600 V AC or higher) at the frequency between 50-200 kHz. The AC sinusoidal voltage at the frequency between 50-200 kHz is the output power from the power supply to the EMAT guided wave sensor.

The output filter may be a LCC filter.

The output filter may include a damping resistor added in parallel to a load of the output filter.

The power supply may further include damping resistors respectively added in series with a DC link of the DC/AC inverter.

The power supply may further include extra Miller capacitors respectively connected between a drain terminal and a gate terminal of the power switches of the DC/AC inverter.

The power supply may further include a plurality of Zener diodes respectively connected between a gate terminal and a source terminal of the power switches of the DC/AC inverter.

The power supply may further include a DC link capacitor positioned between the DC/DC converter and the DC/AC inverter. The DC link capacitor provides pulse power to the DC/AC inverter and is charged with a limited low current from the DC/DC converter during sleeping periods.

The power supply may further include a plurality of clamping capacitors in parallel with the DC link capacitor.

The DC/AC inverter may have a full H-bridge configuration having four SiC Mosfet power switches or a half-bridge configuration having two SiC Mosfet power switches.

The DC/DC converter may include a front H-bridge having four Silicon (Si) Mosfet power switches and a rear H-bridge having four Silicon (Si) Mosfet power switches. The power supply may further include an input capacitor positioned in front of the DC/DC converter and connected in parallel with the front H-bridge of the DC/DC converter. The power supply may further include an output capacitor positioned at the output of the DC/DC converter and connected in parallel with the second stage H-bridge of the DC/DC converter.

The DC/DC converter may be a flyback boost converter. The input capacitor of this topology is relatively larger because of discontinuous input current. The output may have a DC capacitor.

The power supply may further include a gate driver IC for each power switch of the DC/AC inverter to amplify gate signals to drive gates of the power switches of the DC/AC inverter. The power supply may further include gate resistor circuits respectively for the power switches of the DC/AC inverter and the gate driver IC is connected to the gate resistor circuits. The power supply may further include an opto-isolator coupler placed connected to the gate driver IC. The power supply may further include an isolated DC/DC converter to supply power to the gate driver IC.

The power supply may include a first filter, a second filter, and a switch for implementing one of the first filter and the second filter as the output filter of the power supply. The system may further include a controller to control the switch to select the first filter as the output filter of the power supply when the EMAT sensor is an EMAT normal beam sensor and to control the switch to select the second filter as the output filter of the power supply when the EMAT sensor is an EMAT guided wave sensor.

The first filter may be a LCC filter and the second filter may be a LCC filter with L and C values of the first filter being different than L and C values of the second filter.

The first filter may be a LCC filter and the second filter may be a LC filter.

The EMAT system may further include a controller to control the power switches of the DC/AC inverter using pulse width modulation (PWM) for the DC/AC inverter to invert the boosted DC voltage into the AC square voltage for when the EMAT sensor is an EMAT normal beam sensor and to control the power switches of the DC/AC inverter using either PWM or sinusoidal pulse width modulation (SPWM) for the DC/AC inverter to invert the boosted DC voltage into the AC square voltage for when the EMAT sensor is an EMAT guided wave beam sensor.

In an embodiment, a system for inspecting a pipe includes a robot movable along a pipe, an EMAT sensor mounted on the robot to be adjacent a portion of the pipe, and a power supply mounted on the robot and physically connected to the EMAT sensor for supplying output power to the EMAT sensor. The power supply includes a DC/DC converter to boost an input DC voltage into a boosted DC voltage, a DC/AC inverter having Silicon Carbide (SiC) Mosfet power switches to invert the boosted DC voltage into an AC square voltage, and an output filter to filter the AC square voltage into an AC sinusoidal voltage. The AC sinusoidal voltage is the output power from the power supply to the EMAT sensor. No transformer is used on the AC side to boost the voltage.

In an embodiment, a system for inspecting a part includes an unmanned aerial vehicle (UAV) flyable over a part at a separation distance, an EMAT sensor mounted on the UAV, and a power supply mounted on the UAV and physically connected to the EMAT sensor for supplying output power to the EMAT sensor. The power supply includes a DC/DC converter to boost an input DC voltage into a boosted DC voltage, a DC/AC inverter having Silicon Carbide (SiC) Mosfet power switches to invert the boosted DC voltage into an AC square voltage, and an output filter to filter the AC square voltage into an AC sinusoidal voltage. The AC sinusoidal voltage is the output power from the power supply to the EMAT sensor. No transformer is used on the AC side to boost the voltage.

DETAILED DESCRIPTION

Detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Figure 1:
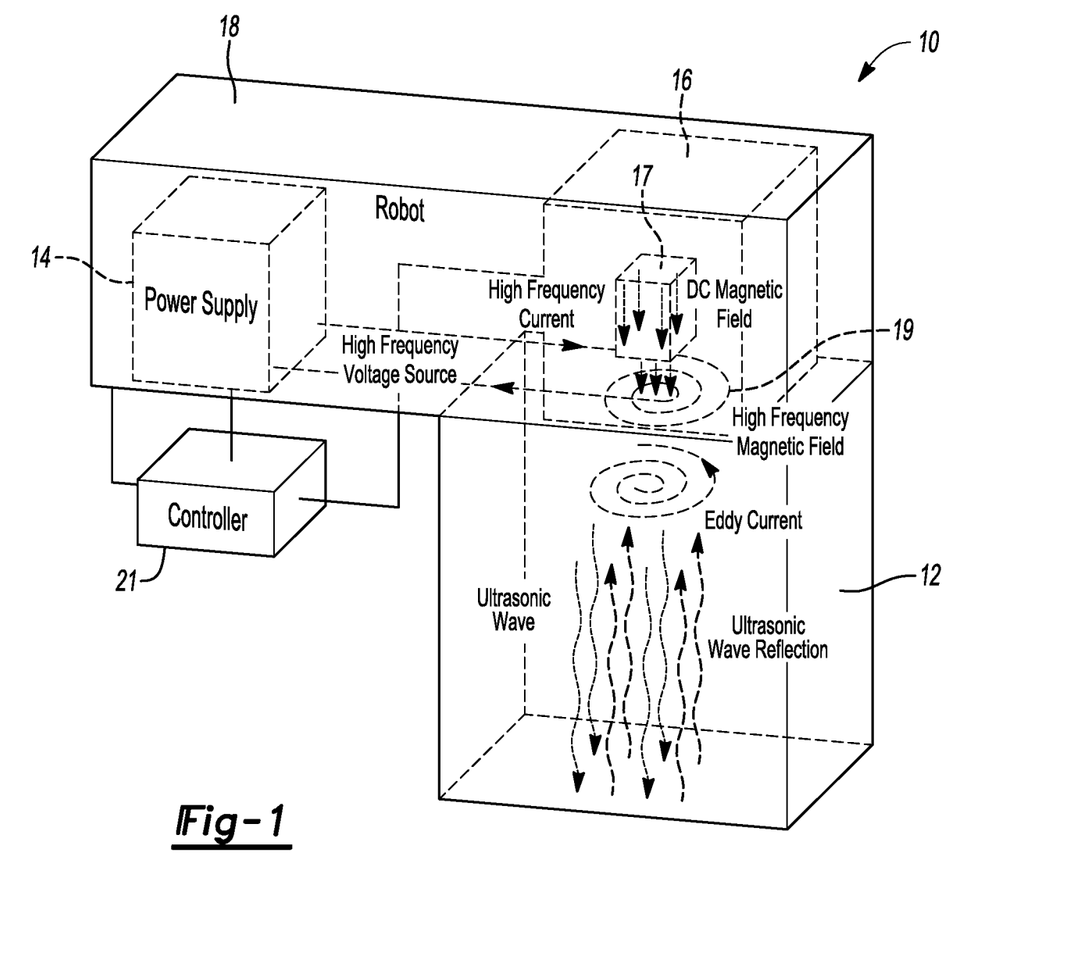
FIG. 1 illustrates a block diagram of a system for ultrasonic inspection of a pipe, the system having a power supply, an electromagnetic acoustic transducer (EMAT) sensor in the form of an EMAT normal beam sensor, and a robot that can access the pipe.

Referring now to FIG. 1, a system 10 for ultrasonic inspection of a part to be inspected is shown. The part to be inspected is in the form of a pipe 12. System 10 includes a power supply 14, an electromagnetic acoustic transducer (EMAT) sensor 16, and a robot 18. EMAT sensor 16 as shown in FIG. 1 is an EMAT normal beam sensor. Robot 18 can access (e.g., move throughout and physically against/near) pipe 12. Power supply 14 and EMAT sensor 16 are mounted on robot 18. EMAT sensor 16 includes a permanent magnet 17 and an electrical coil 19. Power supply 14 is connected to electrical coil 19. Power supply 14 outputs electrical power to electrical coil 19 which in combination with permanent magnet 17 causes EMAT sensor 16 to generate an ultrasound in pipe 12. The ultrasound travels through pipe 12 and a portion of the ultrasound reflects backward to EMAT sensor 16.

A controller 21 (e.g., an electronic processor such as a computer) in communication with EMAT sensor 16 detects wall thickness, wall loss, and defects such as cracks of pipe 12 based on the transmitted and received ultrasound. Controller 21 is further in communication with power supply 14 to control its operation in outputting power to EMAT sensor 16. Controller 21 is further in communication with robot 18 to control its operation.

Power supply 14 is a low distortion, high power density, pulse power supply having the following features: a first feature of being able to output proper power to (i) EMAT normal beam sensors and (ii) EMAT guided wave sensors; a second feature of being designed to enable its integration installation on different types of robots for pipes with different configurations or diameters; and a third feature of having an enhanced waveform quality of its output power for improving measurement efficiency.

Power supply 14 has the first feature of being able to provide proper output power to EMAT normal beam sensors and EMAT guided wave sensors as the voltage range and frequency range of the output power of the power supply is 0-600 V AC peak and 50 kHz to 1.5 MHz. The output power voltage range is sufficient for both types of EMAT sensors. The output power frequency range is sufficient for EMAT normal beam sensors which function with output power having a frequency range on the order of 1.5 MHz. The output power frequency range is also sufficient for EMAT guided wave sensors which function with output power having a frequency range on the order of 50 kHz to 200 kHz.

Power supply 14 has the second feature of being designed to enable its integration installation on different types of robots for pipes with different diameters or configurations to meet applicable size requirements. EMAT sensor 16 will typically be mounted on robot 18 to perform measurements from the inner surface of pipe 12. Thus, the best installation place of power supply 14 is on robot 18 and near EMAT sensor 16. The high-power density aspect of power supply 14 reduces the space occupation of the power supply. This is beneficial for robot and pipe configurations (e.g., diameter sizes) in which space is limited after accounting for robot 18. Power supply 14 has a relatively small size such that it can be used as a standard component to be installed on different types of robots for different pipe configurations.

Power supply 14 has the third feature of having an enhanced waveform quality of its output power. This improves the quality of the ultrasound caused to be generated by EMAT sensor 16 from the output power. Consequently, the measurement efficiency in the detection of wall thickness, wall loss, and defects of pipe 12 based on the transmitted and received ultrasound is improved.

In regards to the third feature, a problem with conventional power supplies for EMAT sensors is voltage ringing at the end of the waveform of the output power. For an EMAT normal beam sensor, this limits the minimum thickness that can be measured because at a thickness smaller than the minimum the echo overlaps the source. For an EMAT guided wave sensor, this increases the dead zone. Power supply 14 includes an output (resonant) filter from which the output power is supplied to EMAT sensor 16. Damping is added in the output filter of power supply 14 to reduce the ringing period to less than a quarter fundamental period.

Further in regards to the third feature, another problem with conventional power supplies is poor output power waveform quality. This affects the readable rate of the echoes. A low harmonics sinusoidal source waveform results in a low harmonics echo waveform. Thus, the echo can be better differentiated from distortion or noise. Conventional power supplies which use a step-up MHz transformer at their output have a significantly distorted output power waveform. This is because the step-up MHz transformer presents complex LC network characteristics at MHz range. As described in greater detail herein, power supply 14 does not employ a transformer at its output and instead employs a high voltage inverter and output filter as the last stage of which the output voltage is close-loop controlled.

Electrical Requirements of the Power Supply

In embodiments, power supply 14 is to generate an output power having a ±600 V AC sinusoidal voltage at a 1.5 MHz frequency from an input power having a 24 V DC voltage (or a 48 V DC voltage). Power supply 16 generates the output power as pulses. EMAT sensor 16 uses the output power (i.e., discrete pulses) from power supply 14 to generate (discrete) ultrasound echoes in pipe 12.

In embodiments, the output power is set at 8 kW peak and 8 W average. The output current is set at 30 A peak and 0.6 A RMS. The output voltage, current, and power requirements are targeted at generating larger eddy current on the surface of walls of pipe 12 to enhance the echo amplitude. The energy transfer efficiency from magnetic vibration to ultrasonic is extremely low and therefore the source voltage is kilovolts whereas the echo voltage is in microvolts.

In embodiments, the frequency of the output power is set at 1.5 MHz when EMAT sensor 16 is an EMAT normal beam sensor. The output power having the relatively high 1.5 MHz frequency causes the echo packet to be narrow which results in proper time-of-flight (TOF) detection capability, especially for thinner pipe walls. The ultrasonic radiation efficiency is also higher when the output power has the 1.5 MHz frequency.

In embodiments, the frequency of the output power is set in the range of 50-200 kHz when EMAT sensor 16 is an EMAT guided wave sensor. Power supply 14 can provide an output power having a 50-200 kHz frequency as the power supply can handle the more difficult task of providing an output power having a 1.5 MHz frequency. Therefore, as power supply 14 can satisfy the requirements of EMAT normal beam sensors, the power supply can be adapted to EMAT guided wave sensors.

Pulse repetition frequency of power supply 14 refers to the frequency the pulse is repeated. This is also the frequency at which independent measurement are taken. The lower the pulse repetition frequency, the lower average power required by EMAT sensor 16 from power supply 14. The lower average power from power supply 14, the smaller size the power supply can achieve. Theoretically, for thickness measurement purpose, one pulse is enough. However, to better differentiate the echo and the noise, several more pulses may be needed. Therefore, in embodiments, one to five cycles for each measurement is the requirement for power supply 14. The sleeping period refers to the time during two independent measurements, which is at least five micro-seconds in embodiments.

Main-bang refers to the time duration of one cycle source waveform, which is required to be smaller than five microseconds at 1.5 MHz frequency, based on the minimum pipe thickness that EMAT sensor 16 is to measure. If it is transferred to the voltage ringing period, then the ringing needs to be smaller than four cycles. The reason is because to differentiate the source and the echo, the ringing cannot overlap the echo pulse. A larger voltage ringing period leads to a larger minimum time difference between the source and the echo, which means a larger minimum measurable thickness. To measure smaller thicknesses, the ringing is to be short. Here the requirement for power supply 14 is less than five microseconds in embodiments.

The THD (Total Harmonic Distortion) of the output power is to be smaller than 5%. This is because the smaller harmonics the source has, the smaller harmonics the echo will have. The echo can then be easier differentiated from noise.

The failure rate of power supply 14 is to be low because robot 18 is to be dragged out of pipe 12 for maintenance each time the power supply fails.

The load of power supply 14 is (i) electrical coil 19 of EMAT sensor 16 and (ii) pipe 12. The load is equivalent to a series resistor ($R_2$) and inductor ($L_2$) (labeled in FIG. 2). The impedance of coil 19 is not the equivalent load impedance. The equivalent load impedance is the impedance of coil 19 taking into account magnetic interference from pipe 12 and permanent magnet 19 during the electrical energy to mechanical vibration transduction. The major component of the load is an equivalent resistor, which consumes the 8 kW peak power. The impedance has a variation range because of lift-off change and different environment condition of measurement points. Power supply 14 is adaptive to the whole load variation range.

Mechanical Requirements of the Power Supply

The size of power supply 14 is to be small enough for the power supply to be installed on robot 18. In this regard, in embodiments, power supply 14 is designed to have an area no larger than 10 cm*10 cm.

Lift-off of EMAT sensor 16 can vary in a certain range, no smaller than 1.5 mm. Thus, power supply 14 is designed to provide a consistent output power at the whole range.

Electrical Circuit Topology of the Power Supply

As described, in embodiments, power supply 14 is to generate an output power having a ±600 V AC sinusoidal voltage at a 1.5 MHz frequency from an input power having a 24 V DC voltage. Difficulties in converting the input power to the requisite output power include raising the voltage from 24 V to 600 V and pushing the AC frequency to 1.5 MHz.

A conventional way of converting the input power to the requisite output power is to: use a DC/DC converter to raise the 24 V DC input voltage to a 100-200 V DC voltage; use a DC/AC inverter to invert the 100-200 V DC voltage into an AC square voltage having a 1.5 MHz frequency; use a filter to convert the AC square voltage into an AC sinusoidal voltage having the 1.5 MHz frequency; and use a step-up MHz transformer to raise the AC sinusoidal voltage to be a ±600 V AC sinusoidal voltage at the 1.5 MHz frequency. The ±600 V AC sinusoidal voltage at the 1.5 MHz frequency is the output power. A problem with this conventional way is that the output power has a relatively large distortion. The output power has a relatively high TOD because of resonance between a winding capacitor and a winding inductor of the step-up MHz transformer.

Figure 2:
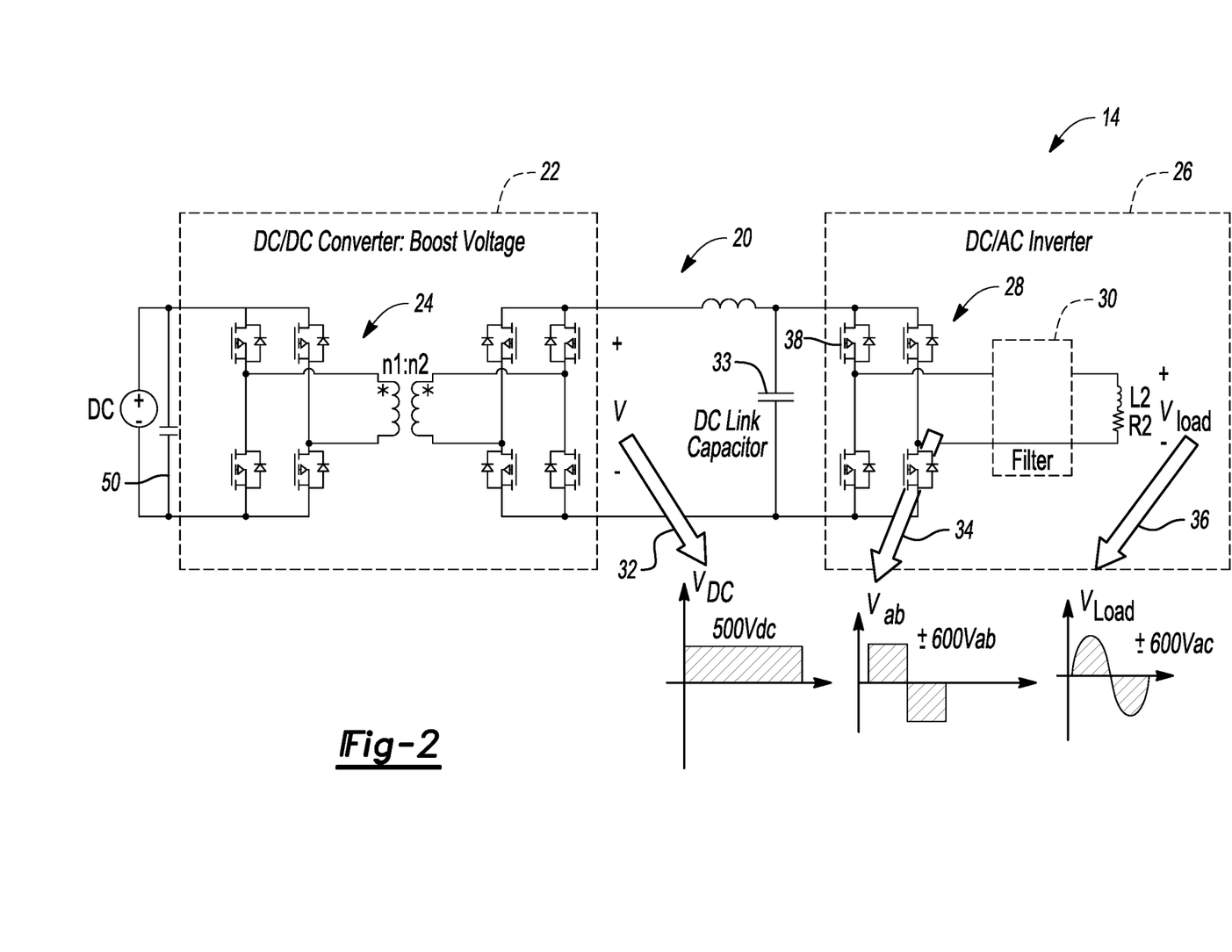
FIG. 2 illustrates a circuit diagram of the circuit topology of the power supply, the circuit topology of the power supply including a DC/DC converter, a DC link capacitor, a DC/AC inverter, and an output filter.

Referring now to FIG. 2, with continual reference to FIG. 1, a circuit diagram of a circuit topology 20 of power supply 14 is shown. Circuit topology 20 of power supply 14 is a two-stage topology. A first stage 22 includes a DC/DC converter 24. A second stage 26 includes a DC/AC inverter 28 and an output (resonant) filter 30. DC/DC converter 24 boosts the 24 V DC input voltage into a 500 V DC voltage as indicated at 32. The 500 V DC voltage charges a DC link capacitor 33 positioned at the front end of DC/AC inverter 28. DC/AC inverter 28 inverts the 500 V DC voltage into a ±600 V AC square voltage at the 1.5 MHz frequency as indicated in 34. Output filter 30 filters the ±600 V AC square voltage into a ±600 V AC sinusoidal voltage having the 1.5 MHz frequency as indicated at 36. The ±600 V AC sinusoidal voltage having the 1.5 MHz frequency is the output power from power supply 14 to EMAT sensor 16.

DC/DC converter 24 uses a soft-switching dual active bridge (DAB) structure. As shown in FIG. 2, the DAB structure includes two H-bridges with a step-up kHz transformer. The second bridge of the DAB structure is exposed to the 500 V DC voltage. The power switches of the second bridge are Silicon (Si) Mosfets which can handle this voltage. As noted, although DC/DC converter 24 is to boost the 24 V DC input voltage into the 500 V DC voltage, the DC/DC converter only provides the relatively low average power of 8 W. To be adapted to a smaller sleeping period, which means higher average power, DC/DC converter 24 is designed to provide an average power of 35 W. Thus, the minimum sleeping period that power supply 14 can operate is 1.25 milliseconds. This means that a maximum 80 Hz pulse repetition frequency is achievable. The output pulse power is supplied only by DC link capacitor 33. First stage 22 functions as a charger for DC link capacitor 33. The charging process lasts for the whole sleeping period.

DC/AC inverter 28 receives this peak power from DC link capacitor 33. As shown in FIG. 2, DC/AC inverter 28 is a full H-bridge inverter having four power switches. One of the power switches is marked with reference numeral 38. The power switches are controlled to switch on and off such as with a 50% duty cycle to invert the 500 V DC voltage into the ±600 V AC square voltage at the 1.5 MHz frequency. The power switches of DC/AC inverter 28 are to handle 1200 V voltages for DC/AC inverter 28 to invert the 500 V DC voltage into the ±600 V AC square voltage. The power switches of DC/AC inverter 28 cannot be implemented with Si Mosfets as Si Mosfets cannot handle 1200 V voltages. The power switches of DC/AC inverter 28 are implemented as Silicon Carbide (SiC) Mosfets which can handle 1200 V voltages. The voltage rating of SiC Mosfets can reach 10 kV and their switching loss is five times less than Si Mosfets. The power switches of DC/AC inverter 28 are implemented as 1.2 kV (or 1.7 kV) SiC Mosfets which can handle 1.5 MHz switching frequency.

Circuit topology 20 of power supply 14 thereby uses a high voltage SiC Mosfet formed H-bridge DC/AC inverter 28. DC/AC inverter 28 directly outputs the ±600 V AC square voltage having the 1.5 MHz frequency. Output filter 30 filters the ±600 V AC square voltage into a ±600 V AC sinusoidal voltage having the 1.5 MHz frequency. As such, in comparison with the described above conventional way of converting the input power to the requisite output power, DC/AC inverter 28 replaces the low voltage DC/AC inverter (which uses Si Mosfet switches) and the step-up MHz transformer.

Advantages of circuit topology 20 of power supply 14 in comparison with the described above conventional way of converting the input power to the requisite output power include the following: lower skin effect, lower conduction losses, and lower switching losses due to lower current; easier to parallel connect DC/DC converter 24 to have higher current; highly developed, highly reliable SiC Mosfet devices are employed in DC/AC inverter 28; and no step-up MHz transformer is used.

As described and will be described in greater detail herein, further advantages of circuit topology 20 of power supply 14 include low THD on the output power, short ringing period after each pulse, easy to implement soft-switching to mitigate risk on voltage breakdown, and small size. A further advantage of circuit topology 20 of power supply 14 is that the load voltage is direct from the output of DC/AC inverter 28, which can be closed-loop controlled. These advantages match EMAT sensor pulse power supply requirements.

In operation, controller 21 controls the power switches of DC/AC inverter 28 using pulse width modulation (PWM) when EMAT sensor 16 is an EMAT normal beam sensor for the DC/AC inverter to generate the ±600 V AC square voltage at the 1.5 MHz frequency. Controller 21 uses 50% duty-cycle PWM instead of sinusoidal pulse width modulation (SPWM) in controlling the power switches of DC/AC inverter 28 when EMAT sensor 16 is an EMAT normal beam sensor because the fundamental frequency of 1.5 MHz is close to the upper frequency limit of 1.2 kV SiC Mosfet switches. If SPWM is used, then the switching frequency is at least several times of the fundamental. However, a disadvantage of the AC square voltage outputted by DC/AC inverter 28 is that it is to be filtered into an AC sinusoidal voltage. But this is overcome by implementing output filter 30 as a LCC resonant filter, as described in greater detail below. The LCC resonant filter enables the soft-switching of the power switches of DC/AC inverter 28.

Thus, controller 21 functions as a PWM controller to DC/AC inverter 28 when EMAT sensor 16 is an EMAT normal beam sensor. In this case, DC/AC inverter 28 outputs the ±600 V AC square voltage having the 1.5 MHz frequency to output filter 30. Output filter 30 filters the ±600 V AC square voltage having the 1.5 MHz frequency into a ±600 V AC sinusoidal voltage having the 1.5 MHz frequency.

When EMAT sensor 16 is an EMAT guided wave sensor the fundamental frequency is 50-200 kHz. The SiC Mosfet power switches of DC/AC inverter 28 have no issue operating at this relatively low frequency range when the 50% duty cycle modulation is utilized. However, output filter 30 is to accommodate the 50-200 kHz fundamental frequency. Although controller 21 could use SPWM in controlling the power switches of DC/AC inverter 28 because the switching frequency capability of the power switches is much higher than the fundamental frequency, 50% duty-cycle PWM in controlling the power switches is still adopted since the soft-switching is to be implemented to reduce the overshoot voltage on the device.

Thus, controller 21 functions as a PWM controller to DC/AC inverter 28 when EMAT sensor 16 is an EMAT guided wave sensor. In this case, DC/AC inverter 28 outputs a ±600 V AC square voltage having the 50-200 kHz frequency to output filter 30. Output filter 30 filters the ±600 V AC square voltage having the 50-200 kHz frequency into a ±600 V AC sinusoidal voltage having the 50-200 kHz frequency. However, as indicated, controller 21 may function as a SPWM controller to DC/AC inverter 28 when EMAT sensor 16 is an EMAT guided wave sensor.

Figure 3A:
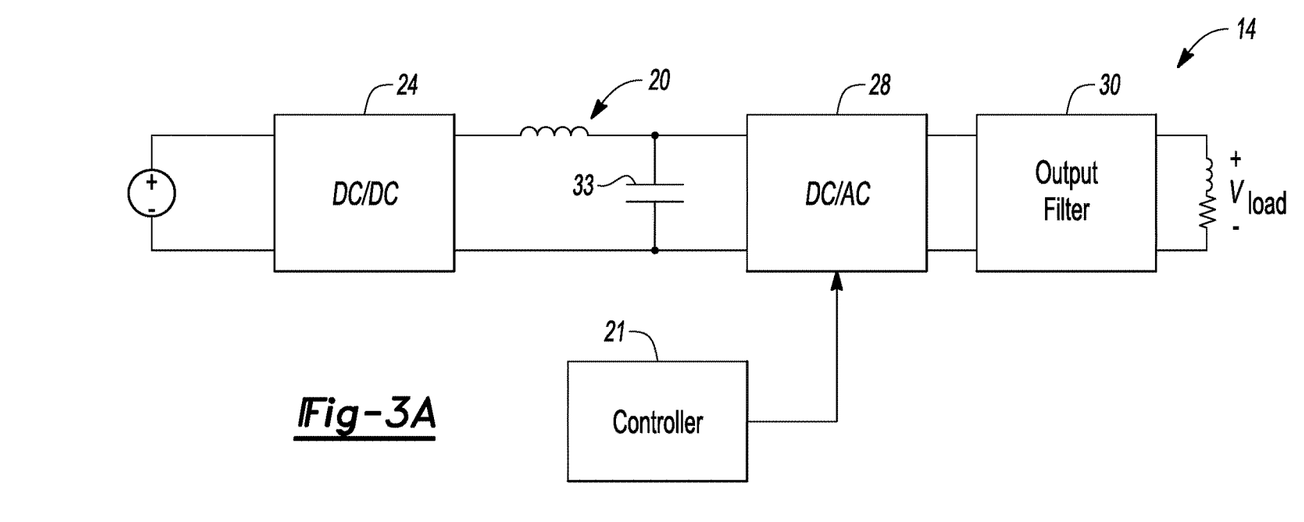
FIG. 3A illustrates a block diagram of the power supply.

Referring now to FIG. 3A, with continual reference to FIGS. 1 and 2, a block diagram of power supply 14 is shown. For a square waveform (e.g., the ±600 V AC square voltage having the 1.5 MHz frequency from DC/AC inverter 28) inputted to output filter 30 the largest harmonic components include the $3^{rd}$ harmonic, which is close to the fundamental component. The filter gain curve is to be equal to unity at the fundamental frequency of 1.5 MHz, but smaller at the $3^{rd}$ harmonic. The ideal case will be that output filter 30 satisfies the gain requirement while maintaining minimum passive component stress. In the definition of filter characteristics, the component stress is proportional to the Q factor. Thus, a low Q factor is desired. A low Q factor can be achieved by using a low resonant inductance.

Comparing several different resonant filters, a LCC output filter is the best candidate for EMAT normal beam sensors. In sum, a benefit of the LCC output filter is to make DC/AC inverter 28 achieve soft-switching (e.g., zero voltage switching) while meeting the design targets of unity gain at switching frequency at different load conditions, enough attenuation at $3^{rd}$ harmonics, and relatively low inductor current stress and low capacitor voltage stress. Therefore, the LCC output filter is adopted as it achieves: low $3^{rd}$ harmonic gain; low inductor and capacitor voltage stress; soft-switching operation; and relatively low output voltage variation range when the load changes.

The design of output filter 30 for EMAT guided wave sensors follows the same procedure as the EMAT normal beam sensors. The Q factor, ratio between resonant frequency and switching frequency, and the ratio between parallel capacitor and series capacitor remain the same. The final L and C values are different than output filter 30 for EMAT bulk wave sensors because the EMAT guided wave sensors have a different fundamental frequency of 200 kHz.

Figure 3B:
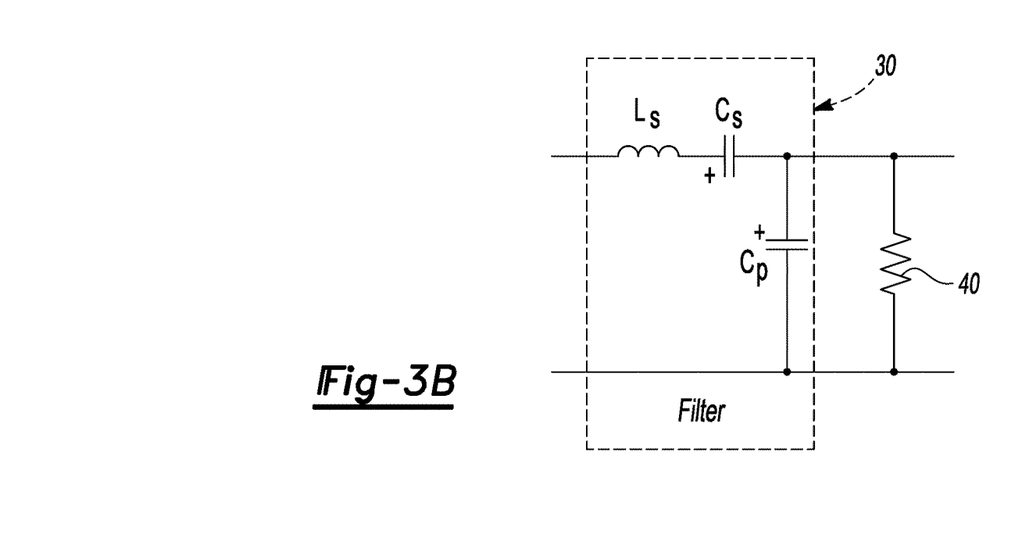
FIG. 3B illustrates a circuit diagram of the output filter of the power supply.

FIG. 3B illustrates a circuit diagram of output filter 30. As shown, output filter 30 is a LCC output filter. Again, the LCC configuration is used for output filter 30 for the following reasons: (1) it has a high attenuation ratio for $3^{rd}$, $5^{th}$, and $7^{th}$ harmonics; (2) its gain can be regulated to be higher than one; and (3) it has low voltage stress on the passive components.

Figure 4:
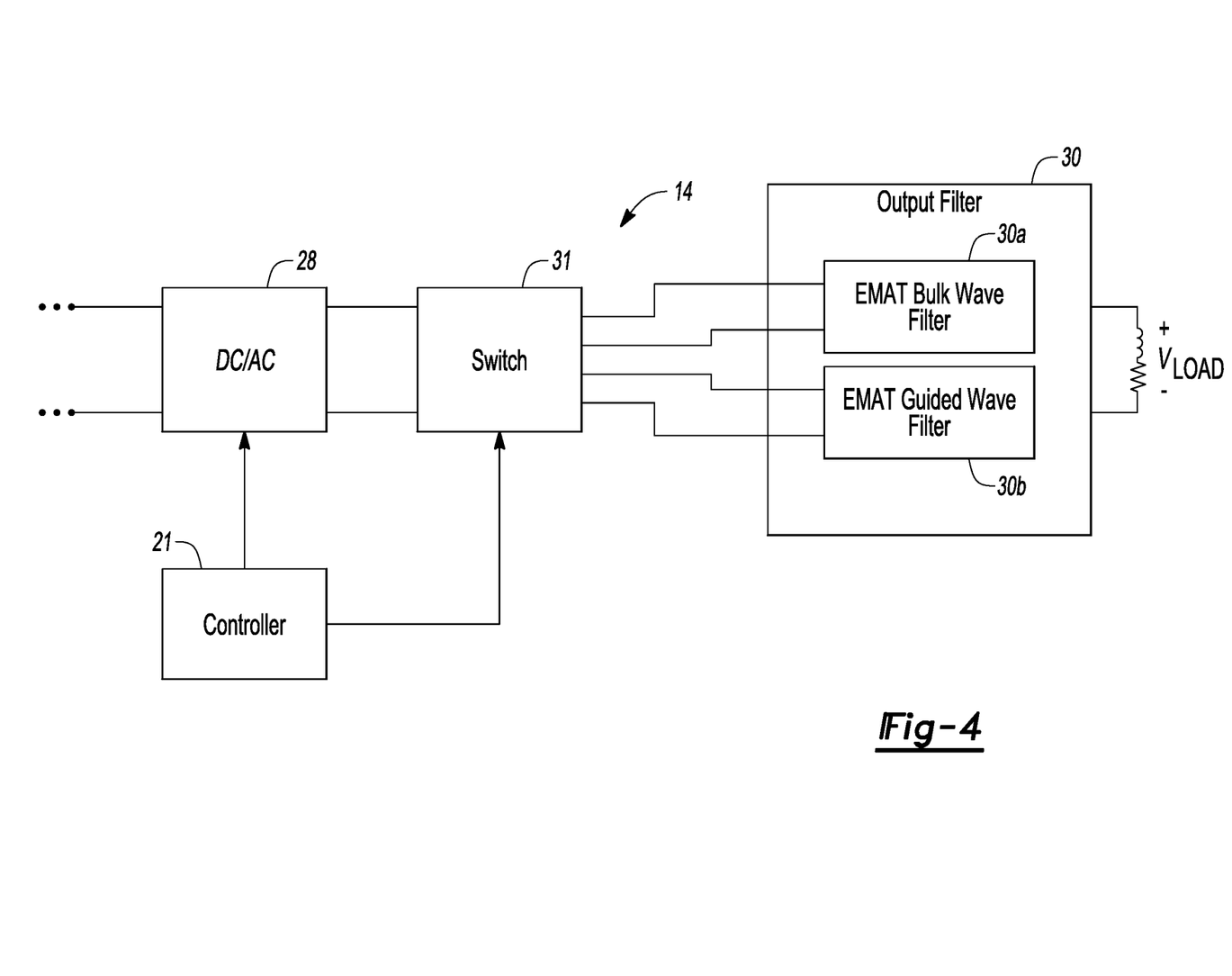
FIG. 4 illustrates a block diagram of the power supply in accordance with another embodiment.

Referring now to FIG. 4, with continual reference to FIGS. 2 and 3A, a block diagram of power supply 14 in accordance with another embodiment is shown. In this embodiment, output filter 30 includes two selectable output filters: a first output filter 30a for when EMAT sensor 16 is an EMAT normal beam sensor; and a second output filter 30b for when EMAT sensor 16 is an EMAT guided wave sensor. Both output filters 30a and 30b are LCC output filters. First output filter 30a has L and C values designed for EMAT sensor 16 being an EMAT normal beam sensor whereas second output filter 30b has different L and C values designed for EMAT sensor 16 being an EMAT guided wave sensor. In other embodiments, output filters 30a and 30b are different types of filters. For instance, in other embodiments, first output filter 30a is a LCC output filter whereas second output filter 30b may be a LC output filter.

As shown in FIG. 4, in this embodiment, circuit topology 20 of power supply 14 further includes a switch 31 for switching between first output filter 30a and second output filter 30b. Switch 31 involves connecting a selected one of output filters 30a and 30b to the output of DC/AC inverter 28. Switch 31 further involves connecting the selected one of output filters 30a and 30b to EMAT sensor 16 connected to power supply 14.

In this embodiment, controller 21 is operable for having switch 31 implement first output filter 30a as the output filter of power supply 14 when EMAT sensor 16 is an EMAT normal beam sensor. As described, controller 21 implements PWM control of the power switches of DC/AC inverter 28 when EMAT sensor 16 is an EMAT normal beam sensor.

Likewise, in this embodiment, controller 21 is operable for having switch 31 implement second output filter 30a as the output filter of power supply 14 when EMAT sensor 16 is an EMAT guided wave sensor. As described, controller 21 implements PWM control of the power switches of DC/AC inverter 28 when EMAT sensor 16 is an EMAT guided wave sensor, but could alternatively implement SPWM control of the power switches of the DC/AC inverter.

Mechanical Size of the Power Supply

As described herein, the physical size of power supply 14 is smaller than conventional power supplies for EMAT sensors for the following reasons. Circuit topology 20 of power supply 14 has only two stages with the space for a step-up MHz transformer being eliminated. A higher DC link voltage is at the output of DC/DC converter 24, which means higher voltage diodes are employed in the second H-bridge of the DC/DC converter. However, the diode size is negligible compared to the Mosfet power switches of DC/DC converter 24 so the size will not increase. DC/AC inverter 28 has a smaller size than conventional DC/AC inverters of power supplies for EMAT sensors because at the same voltage and current ratings the SiC Mosfet power switches of DC/AC inverter 28 are much smaller than Si Mosfet power switches. Further, discrete SiC Mosfet power switches may be used as the power switches of DC/AC inverter 28 instead of a SiC Mosfet device module to further reduce the physical size of power supply 14.

Reducing Main Bang of the Power Supply (Reduce Transient Resonance at End of Pulse)

The cause of residue resonance after power supply 14 is switched off is the remaining energy stored in output filter 30. When the load is off, the resonance in output filter 30 still exists. This resonance cannot be quickly damped as no parallel load resistor exists to consume the energy. Therefore, a damping resistor 40 is added in parallel to the load of output filter 30 (shown in FIG. 3B). When the load is off, damping resistor 40 damps the energy stored in the resonance capacitor and inductor of output filter 30. Further, to reduce the power loss on damping resistor 40, a Mosfet device can be added in series with the damping resistor and controlled to be turned on just before the end of the last pulse in each active period.

The value of damping resistor 40 is selected to satisfy the following conditions: small enough to damp energy stored in the resonance capacitor and inductor of output filter 30 within the main-bang time limit, but not too small as it will consume more power and bring the output voltage down. In embodiments, damping resistor 40 having one to two times the load impedance is implemented.

Reducing Voltage Overshooting of the Power Supply

The main strategy to reduce voltage overshooting is to use soft-switching technique for DC/AC inverter 28. However, for the first pulse, soft-switching cannot be implemented due to the small start-up load current. Accordingly, in embodiments, a damping resistor is added in the DC link loop to damp the resonance peak on the Vds caused by hard switching.

The soft-switching of DC/AC inverter 28 refers to the zero-voltage turn-on for the SiC Mosfet power switches of the DC/AC inverter. The zero-voltage turn-on can reduce the switching loss for these power switches, make the Vds rising edge continuous and smooth, thus no voltage overshooting caused by Vds step change, and reduce EMI significantly due to the smooth voltage rising edge.

Figure 5A:
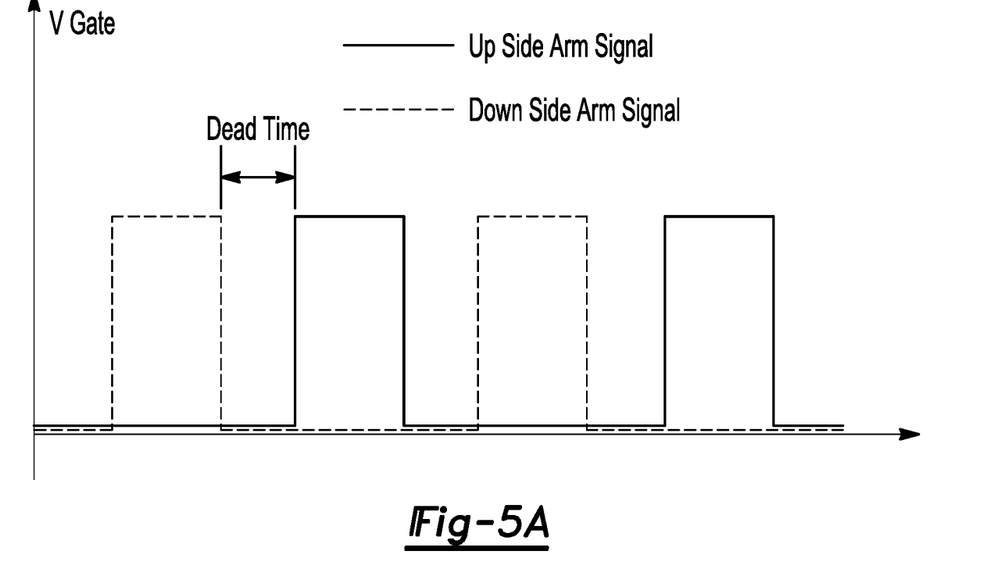
FIG. 5A illustrates a timing diagram depicting operation of the power switches of the DC/AC inverter of the power supply.
Figure 5B:
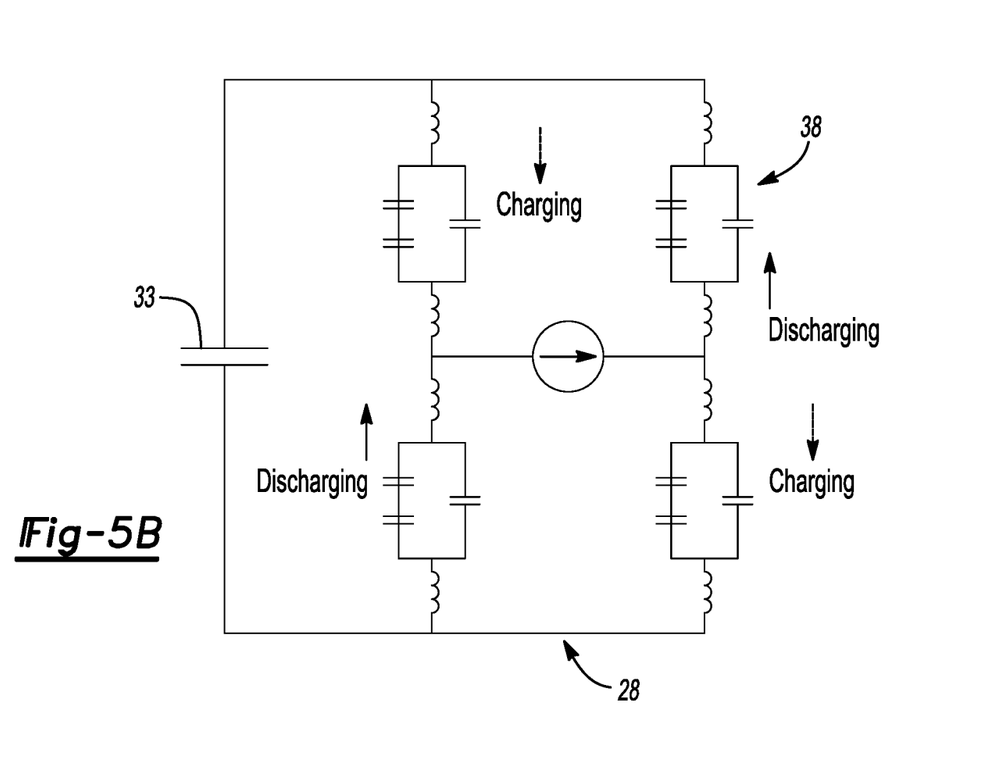
FIG. 5B illustrates a block diagram depicting operation of the power switches of the DC/AC inverter of the power supply.

Referring now to FIGS. 5A and 5B, a timing diagram and a block diagram depicting operation of the SiC Mosfet power switches of DC/AC inverter 28 are shown, respectively. FIGS. 5A and 5B are indicative of the equivalent circuit for junction capacitor charging/discharging during the dead-time.

The process of zero-voltage turn-on will be explained with reference to FIGS. 5A and 5B. First, when the upper switch is turned off, the lower switch needs to wait for a dead-time to be turned on. The junction capacitors of two complementary switches on the same phase leg are in parallel and they are in series with the junction capacitor in the other phase leg. DC link capacitor 33 is like a short circuit because it is much larger than the junction capacitor. Similarly, capacitor(s) and inductor of output filter 30 is like a short circuit because it is much larger than the junction capacitor. As such, the load current charges the junction capacitor of the upper switch but discharges the junction capacitor of the lower switch for the first leg, and does the opposite for the second leg. At the same time, there is parasitic inductor in series with the junction capacitor. From the beginning of the dead-time to the end of the dead-time, the voltage of the junction capacitor for the upper switch is charged from zero to the full DC voltage and the voltage of the junction capacitor for the lower switch is discharged from the full DC voltage to the zero voltage. Thus, when the turn-on edge of the lower switch comes, the diode of the lower switch automatically turns on because the current is negative (which is in the direction of the diode current). From this moment, the voltage on the SiC Mosfet power switch is clamped to zero. The load current keeps increasing until zero. When the load current crosses zero, the current changes from the diode to the SiC Mosfet power switch naturally without any transient. At this SiC Mosfet power switch turn on, the power switch is turned on zero voltage. The other three SiC Mosfet power switches of DC/AC inverter 28 are all turned on at zero voltage and they can be analyzed similarly.

Therefore, the implementation of zero voltage switching relies on the following three factors: the output current of the H-bridge of DC/AC inverter 28 needs to lag the gate on signal; the turn off current at the gate off edge needs to be large enough in order to charge the junction capacitor to full voltage during the dead time; and the dead-time needs to be designed appropriately in order to switch on the device exactly at or a little after the junction capacitor of the other device in the same phase leg is charged to the DC link voltage.

Reducing Vds Overshooting in the Soft-Switching

Even when the soft-switching is implemented, the overshooting still exists due to the high dv/dt of the SiC Mosfet power switches. The dv/dt of SiC Mosfet power switches is four to five times faster than the Si Mosfet power switches. Another reason for the overshooting is the parasitic string inductance in dc link and the interconnection point of devices.

Figure 6:
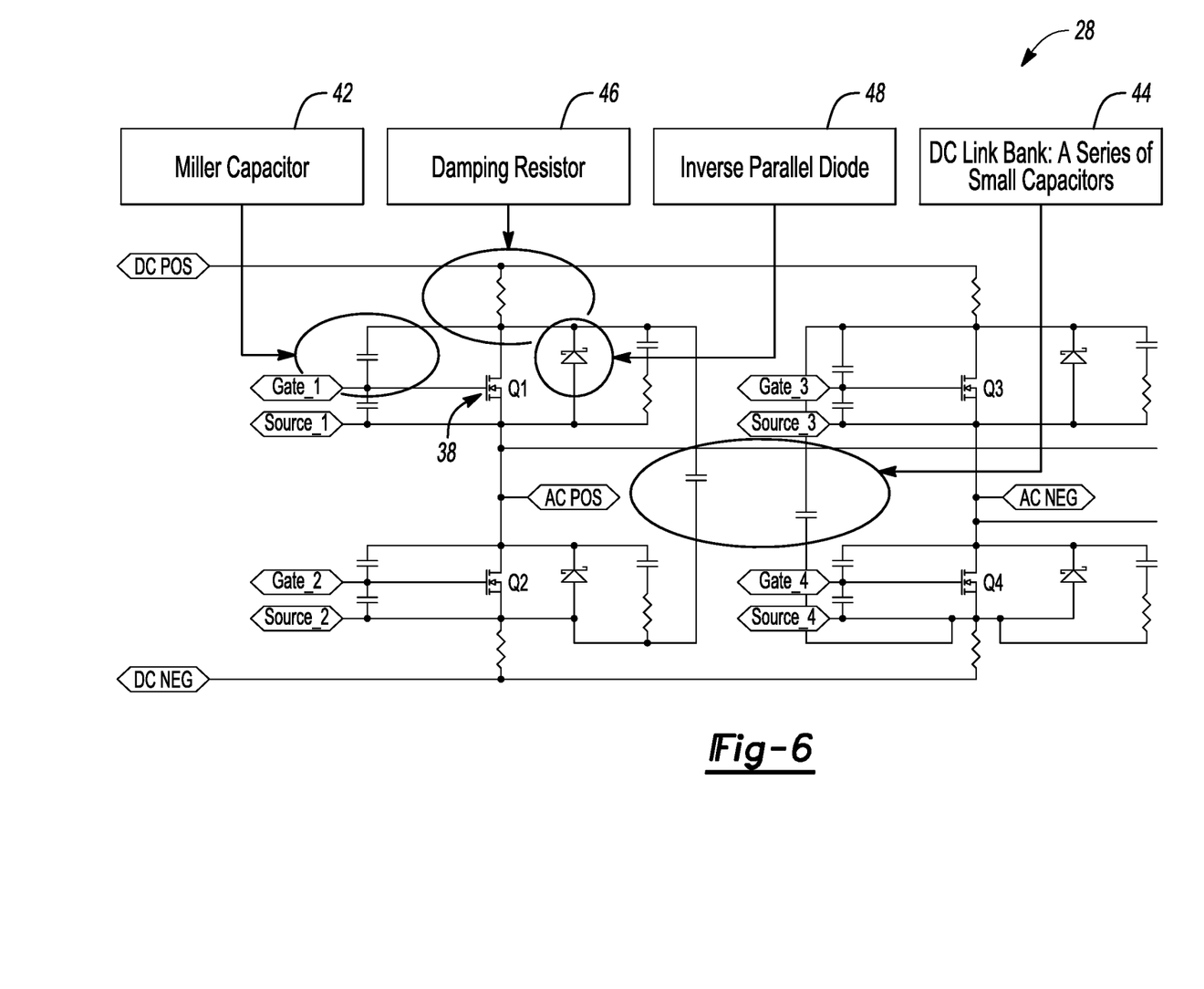
FIG. 6 illustrates a detailed circuit diagram of the DC/AC inverter of the power supply in accordance with certain embodiments.

Referring now to FIG. 6, with continual reference to FIG. 2, a detailed circuit diagram of DC/AC inverter 28 in accordance with certain embodiments is shown. In these embodiments, methods to reduce Vds overshooting include: providing a Miller capacitor, indicated at 42, for each SiC Mosfet power switch to reduce dv/dt; laying out carefully to reduce the dc link loop string inductance; and adding small ceramic capacitors, indicated at 44, in parallel with DC link capacitor 33. The Miller capacitors (e.g., ceramic capacitors) for the SiC Mosfet power switches are connected between the drain and the gate of the respective SiC Mosfet power switch. The reason for adding the small ceramic capacitors in parallel with DC link capacitor 33 is that the DC link capacitor has a series ESL (inductor) which makes the capacitor impedance more towards inductive at high frequency. With a group of the small ceramic capacitors installed in parallel with DC link capacitor 33, a small ESL of the small ceramic capacitors will be parallel to the large ESL of DC link capacitor 33 thereby reducing the total ESL significantly. Experimental observation has shown that the overshooting during soft-switching is reduced significantly after adding the Miller capacitors. In sum, the Miller capacitance is increased to slow down the dv/dt and to reduce stray inductance in the loop by layout and parallel DC capacitors to reduce the Vds overshooting.

Reducing Vds Overshooting for the $1^{st}$ Pulse Hard-Switching

With continual reference to FIGS. 5A, 5B, and 6, the first pulse of the five pulses experiences hard-switching at turn on because the load current at the first pulse is too low. This low current is not enough to charge the junction capacitor of the complementary power switch to the full voltage within the dead-time. In the middle of the dead-time, the resonance peak appears and the voltage cannot rise further. This is a specific challenge for power supply 14 as it starts every five milliseconds in embodiments. At each start pulse, hard-switching happens. During this hard-switching dead-time, the junction capacitor voltage is charged to some level which is not as high as the full voltage, and then the other power switch is turned on, which forces the voltage on this power switch to jump from that level to the full voltage. This voltage jump stimulates the resonance between the junction capacitor and the parasitic inductance in the dc link and phase leg loop, which brings the voltage overshooting on the off device in the phase leg. The amplitude of the voltage shooting depends on the dv/dt of this voltage jump. This dv/dt cannot be reduced by adding a Miller capacitor because it is a forced dv/dt. In the opposite, a small junction capacitance is needed to make the initial voltage level closer to the full voltage level. However, this will make the other pulses lose the soft switching benefits.

Accordingly, in certain embodiments, damping resistors, one being labeled with reference numeral 46 in FIG. 6, are added in series with the dc link resonance loop to reduce the voltage overshooting at the first pulse hard-switching. Damping resistors 46 should not have too large a resistance because the voltage will drop across these resistors. In certain embodiments, damping resistors are one ohm resistors.

Reducing the Power Switch Gate Voltage Mis-Trigger and Overshooting

During the switching of SiC Mosfet power switches of DC/AC inverter 28, two risks of the power switch gate voltage exist. One risk is the gate voltage rise at off state when the hard-switching happens. The other risk is the negative gate voltage overshooting when the negative dv/dt happens. With reference to FIG. 6, solutions provided by certain embodiments to address these risks will be explained.

The cause for the first risk is as follows. When hard-switching happens (referring to the first pulse), the power switch voltage is forced to jump so the associated Miller capacitor 42 experiences a high dv/dt. Thus, the current in the associated Miller capacitor 42 is larger than usual. Also at this process, the current of the associated Miller capacitor 42 flows from the drain to the gate of the power switch. This excessive Miller current charges the gate capacitance Cgs to make it rise when it should be clamped at a negative level. If this voltage rises to the threshold turn on voltage, then the power switch that should be turned off will turn on at this moment and the shoot through in the phase leg will happen.

The cause for the second risk is as follows. When the turn off power switch junction capacitor is being charged by the load current during the dead-time the other complementary power switch experience a negative dv/dt. This negative dv/dt generates a Miller capacitor current flow from the gate to the drain of the power switch. This Miller capacitor current is partly from the gate drive power supply but mainly from the Cgs. Thus, the Cgs will be discharged during this negative dv/dt dead-time. Since the Cgs voltage is already clamped to negative voltage during this dead-time (not turned on yet) this discharging will make the Cgs voltage drop further to a more negative value. The negative clamping voltage is usually set at −5 V to avoid mis-triggering. It only has 5 V redundancy to the device negative voltage breakdown limit of −10 V. Thus, the negative overshooting should not exceed 5 V.

The strategy adopted in embodiments to solve the first risk is to appropriately design Miller capacitors 42 (i.e., reduce value) to limit the Miller capacitor current during the hard-switching period. Thus, the extra Miller capacitance is designed to a tradeoff between the device dv/dt and the gate voltage mis-trigger.

The strategy adopted in embodiments to solve the second risk is to add a Zener diode, indicated at 48 in FIG. 6, to the gate and source terminals of each SiC Mosfet power switch. Zener diode 48 is to clamp the negative voltage to −10 V (i.e., the lower limit of the device).

Component Selection of the Circuit Topology of the Power Supply

In embodiments, the SiC Mosfet power switches of DC/AC inverter 28 are to be selected from SiC Mosfet power switches which satisfy the following criteria: the voltage rating is at least two times the actual voltage stress in operation (the actual stress is 500 V); the pulse current rating is at least 1.5 times the actual pulse current in operation (the actual pulse current is 60 A); and the turn on and turn off time is much smaller than the fundamental period of 1.5 MHz (650 microseconds).

In embodiments, DC link capacitor 33 is to be selected from capacitors which satisfy the following criteria: the voltage rating is at least 1.5 times larger than the operating voltage of 500 V; the capacitance is larger than a value to limit the voltage drop at the pulse power period to 10% and is smaller than a value to make sure the small rated output current of DC/DC converter 24 can charge back to 500 V within the sleeping period (five milliseconds); the pulse current (dv/dt) capability is at least one microsecond as the DC link capacitor is to be able to supply the pulse current required by the load; and RMS current is not high as the sleeping period is five milliseconds (i.e., RMS current is not high since the sleeping period is 1000 times the pulse period).

DC-DC Converter Input Capacitor

With reference to FIG. 2, in embodiments, circuit topology 20 of power supply 14 further includes an input capacitor 50 for DC/DC converter 24. Input capacitor 50 is positioned in front of DC/DC converter 24 and is connected in parallel with the front H-bridge of the DC/DC converter. The RMS current of input capacitor is to be large due to the discontinuous input current of DC/DC converter 24.

Gate Driver Design

Figure 7:
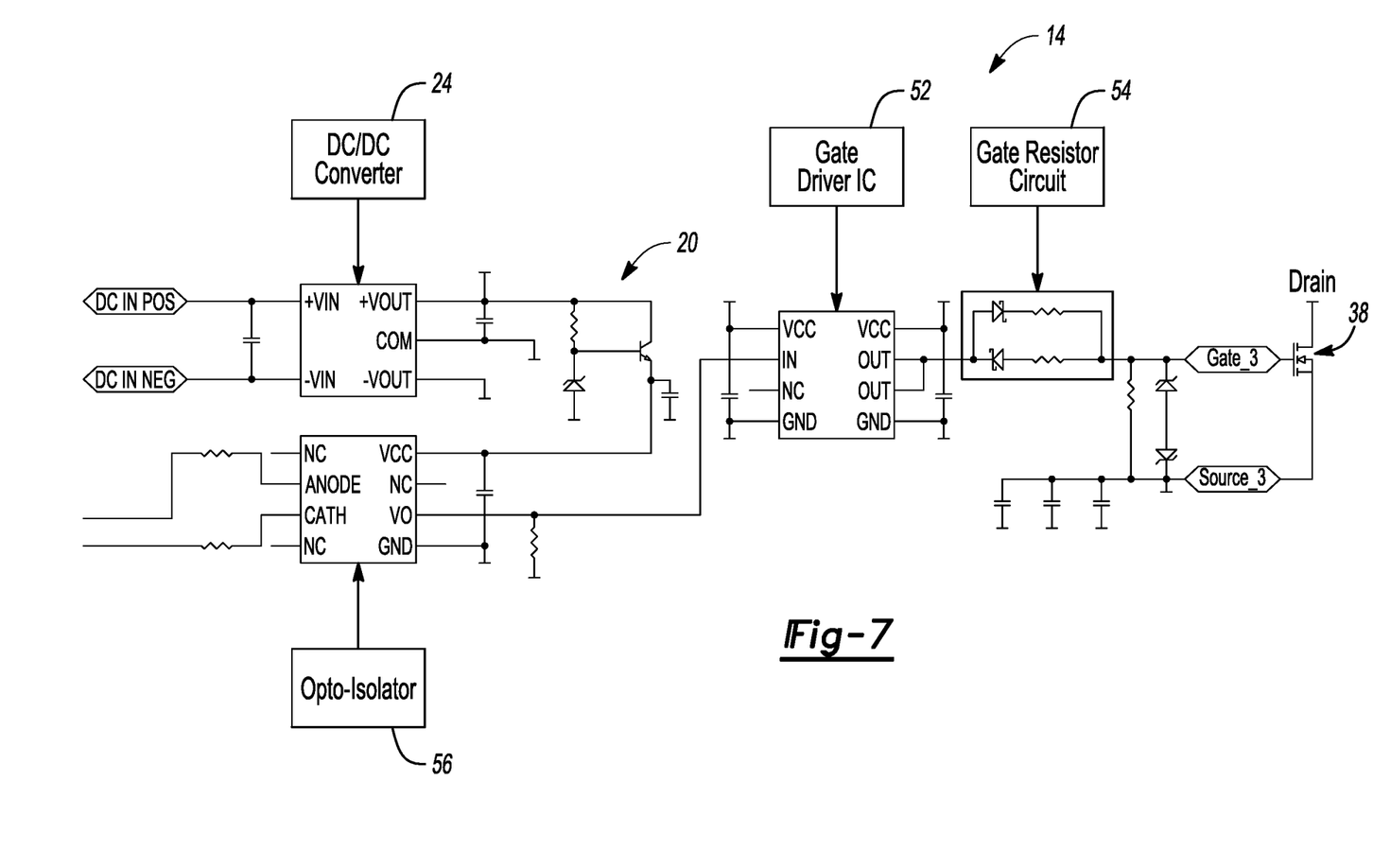
FIG. 7 illustrates a detailed circuit diagram of the circuit topology of the power supply in accordance with certain embodiments.

Referring now to FIG. 7, with continual reference to FIGS. 2 and 6, a detailed circuit diagram of circuit topology 20 of power supply 14 in accordance with certain embodiments is shown. The detailed circuit diagram shows the schematic of the gate driver circuit. A key component is a gate driver IC 52, which is part of controller 21. Gate driver IC 52 amplifies the gate signals to drive the gates of the SiC Mosfet power switches of DC/AC inverter 28. Only one of the SiC Mosfet power switches 38 of DC/AC inverter 28 is indicated in FIG. 7. As gate driver IC 52 amplifies the gate signal to drive the gate of power switch 38, the input of the gate driver IC is connected to a gate resistor circuit 54 for power switch 38.

An opto-isolator coupler 56 is placed between the gate signal and gate driver IC 52 to provide signal isolation between the two. The reason for isolation is that the signal circuits for the four power switches of DC/AC inverter 28 share the same ground, but the actual gate signal has a high voltage difference. Specifically, opto-isolator coupler 56 is a current driven opto-coupler. As such, a designed resistor is placed before it. Another input of gate driver IC 52 is a power source. This also needs to be isolated from the power source of the other power switches. Thus, DC/DC converter 24 is to be a high voltage isolation 24~20/−5 V DC/DC converter which is connected to the voltage supply pin of gate driver IC 52. The output of gate driver IC 52 is connected to the gate and source terminals of power switch 38 through the gate resistor. This gate resistor is selected to satisfy the turn on/off time constant and the gate driver IC capacity. A group of capacitors for the source is placed closed to the Mosfet pin to minimize the gate driver loop length. As mentioned, a Zener diode is placed at the gate and source terminal to clamp the voltage at the maximum and minimum limit.

Requirements for the gate driver include high bandwidth, high frequency, high voltage isolation, high current driven capability, and low time delay. In embodiments, these requirements are met by selecting a high bandwidth gate driver IC, keeping the power dissipation on the gate resistor within the limit, selecting high voltage isolation power supply IC and opto-coupler IC, selecting high current output gate driver IC and small gate resistor, selecting appropriate gate resistor to minimize the time constant and damp the Vgs ringing at the same time, tightening the gate drive loop to minimize the stray inductance, and adding the Zener diode of 25 V/−10 V to clamp the gate voltage.

Accordingly, gate driver IC 52 is selected from gate driver ICs which have a low gate resistance, a short rise and fall time constant, and a high current capability. The type of opto-isolator coupler 56 (e.g., opto-isolator coupler having isolation up to 630 V) and the type of DC/DC converter 24 (e.g., DC/DC converter having 24 V~20 V/−5 V ratio and 5.2 kV isolation level are selected based on the selected gate driver IC 52.

The turn on gate resistor is selected to have a low limit depending on the maximum current gate driver IC 52 can handle and a high limit depending on the device turn-on time constant (RC constant). In embodiments, the resistance of the turn on gate resistor is two ohms.

The turn off fate resistor is selected to have a low limit depending on the maximum current gate driver IC 52 can handle and a high limit depending on (i) the turn-off discharging RC time constant needs to be closed to device turn-off time and (ii) the turn-off Miller capacitor leakage current caused voltage drop on the series turn off resistor needs to be smaller than gate turn on threshold to prevent mis-trigger. In embodiments, the resistance of the turn off gate resistor is two ohms.

Regarding the switching frequency capability evaluation for the gate driver circuit, the turn on and off gate resistor loss inside gate driver IC 52 needs to be smaller than the maximum power dissipation capability of the gate driver IC. The maximum continuous switching frequency of the gate driver circuit is calculated based on the thermal limit to be 200 kHz. However, the gate driver circuit will be operating at the pulse condition instead of continuous. As such, 1.5 MHz switching will not exceed the thermal limit.

Regarding the power source and gate output current requirements, the power source is to be +20 V at turn on and −5 V at turn off because the SiC Mosfet power switches need deep drive (compared to +5 V and 0 V for conventional Si Mosfet power switches). The power source is to be larger than the total gate resistor loss (including the IC and the Mosfet internal gate resistance). The output current of gate driver IC 52 is to be able to drive the SiC Mosfet power switches (which each require at least one ampere to be driven).

Gate Signal Conditioning Circuit Design

Figure 8:
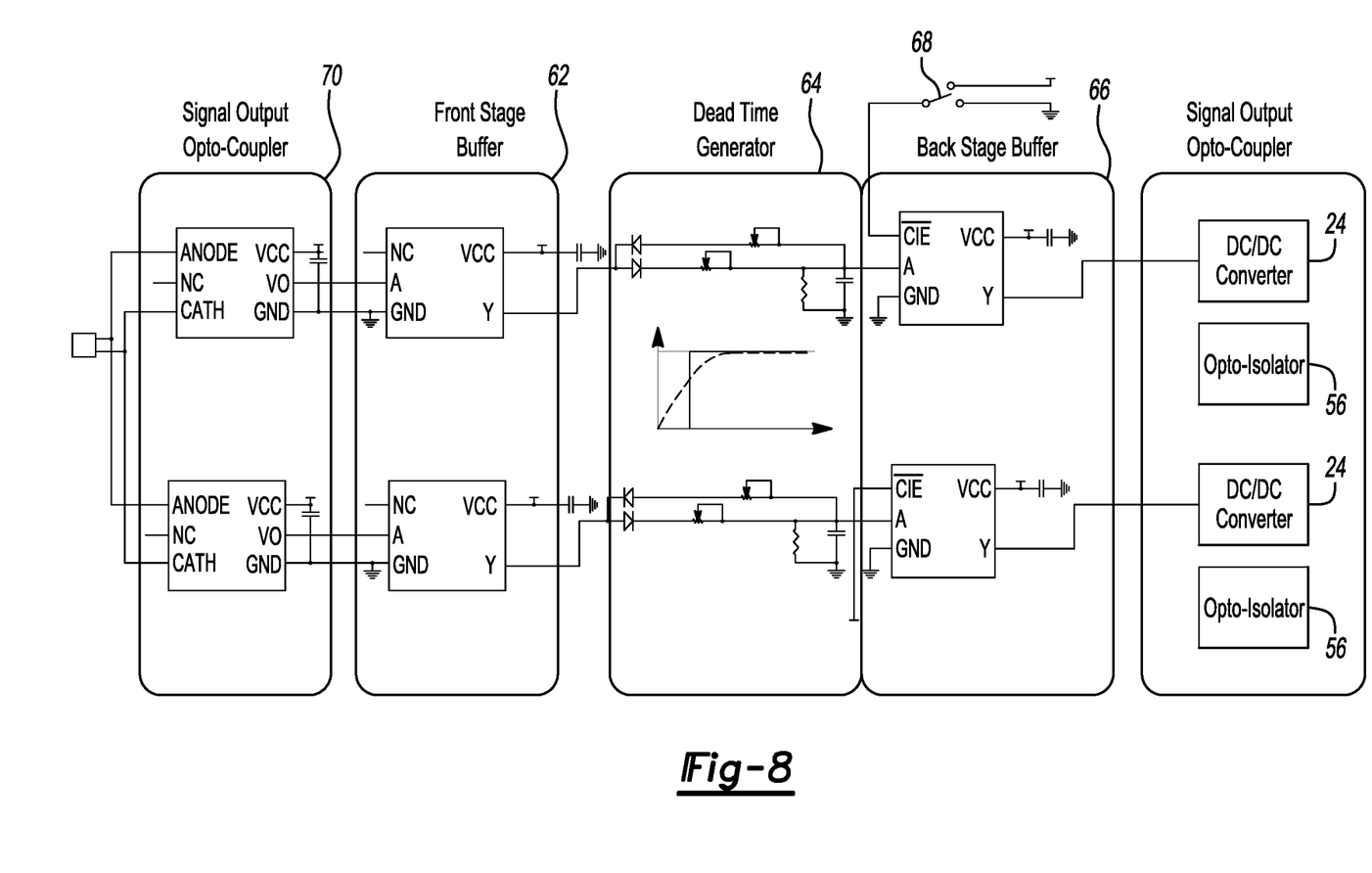
FIG. 8 illustrates a detailed circuit diagram of the gate signal conditioning circuit design of the circuit topology of the power supply in accordance with certain embodiments.

Referring now to FIG. 8, with continual reference to FIGS. 2, 6, and 7, a detailed circuit diagram of the gate signal conditioning circuit design of circuit topology 20 of power supply 14 in accordance with certain embodiments is shown. The gate signal conditioning circuit should implement the following functions: amplify the signal current to drive opto-isolator coupler 56 at the gate driver circuit; have the dead-time regulation function; and can be enabled and disabled.

A front-stage buffer 62 provides the power for a dead time generator 64 (i.e., a RC delay circuit). The RC delay circuit is to generate the dead-time for the upper and lower power switches. The on and off resistors are selected to be variable resistors at (up to five k ohm). Here a low voltage drop diode is used for both on and off path. A back-stage buffer 66 generates the square wave time delay and enlarges the power to drive opto-isolator coupler 56. A SPDT switch 68 is used to disable the signals when the voltage in the circuit does not build up. In addition, a signal input opto-coupler 70 is placed in front of front-stage buffer 62 to isolate the original signal generation circuit (for example, the FPGA) and the signal circuit.

DC/DC Converter Design

As described, in embodiments, DC/DC converter 24 is a 24/500 V converter. DC/DC converter 24 is rated at average power since pulse power is provided by DC link capacitor 33 and the function of the DC/DC converter is to charge the DC link capacitor. A DC/DC regulator having an internal output current control may be provided to limit the capacitor charging surge current.

The design around DC/DC converter 24 may include the following features. A power source interface to stabilize DC/DC converter 24 when the power source has a large inductance. A remote controller, such as implemented by controller 21, to control the on and off state of DC/DC converter 24. It can be designed as an emergency shut down system. An output side circuit to connect the two output lines of DC/DC converter 24 in parallel to provide higher current capability. A common mode noise choke to eliminate common mode current.

PCB Layout

A PCB (printed circuit board) layout of power supply 14 takes into consideration the following issues. Minimizing the gate driver loop to reduce the parasitic inductance, thus reducing gate voltage overshoot due to high dv/dt. Minimizing the DC bus-bar loop to reduce the parasitic inductance, thus reducing DC link overshoot caused by high dv/dt. Creating high voltage isolation barrier between the gate driver power supply, gate signal, DC-DC converter input and output, power switches, output filter capacitor and inductor, and the load. Using four layers of PCB board to shrink the surface area.

Unmanned Aerial Vehicle (UAV) Configuration

In other embodiments, system 10 includes a UAV in place of robot 18. In this case, power supply 14 and EMAT sensor 16 are mounted on the UAV. The UAV is to fly over a part to be inspected at a separation distance.

Additional Variations and Improvements

As described herein, in embodiments, power supply 14 is to output a ±600 AC voltage to an EMAT sensor. The 600 V magnitude of the ±600 V AC output voltage is one example of the magnitude of the AC voltage to be outputted by power supply. In embodiments, power supply 14 is to output a larger AC voltage such as a ±1000 AC voltage to an EMAT sensor. The power switches of DC/AC inverter 28 of power supply 14 are 1.7 kV SiC Mosfet power switches instead of 1.2 kV SiC Mosfet power switches to enable the power supply to output a higher output voltage such as a ±1000 AC voltage. Other changes of power supply 14 to enable the power supply to output a higher AC voltage include changes in the voltage ratings of the passive components and changes in the insulation level of an isolation barrier of the power supply.

In embodiments, output filter 30 is modified to handle higher output voltages such as a ±1000 AC output voltage, of power supply 14. That is, output filter 30 is modified to adapt to the load change in a load range. For instance, instead of being a LCC filter, output filter 30 is modified to be a fourth-order filter or a fourth-order and LC series filter.

In embodiments, power supply 14 includes a FPGA (field-programmable gate array). The FPGA is used on board to perform the dead-time generation functions of dead time generator 64 (shown in FIG. 8). As such, the analog dead time generator (i.e., a RC delay circuit) may be eliminated with the use of FPGA.

In embodiments, the FPGA implements a power and signal enable sequence at the beginning of turning on power supply 14 for protection of the power supply. This startup sequence is to check that the output voltage of power supply 14 is properly generated before turning the signal on. When any fault happens, the DC/DC converter will be switched off as the external signal process is to prevent incorrect external pulse signals.

In embodiments, fault protection circuits are added to power supply 14. The fault protection circuits provide de-saturation protection of power supply 14, an UVLO (under-voltage-lockout) for gate driver and signal power supply, and DC link over-voltage protection. In this case, a gate driver IC having integrated desaturation detection and fault and UVLO status feedback is implemented as the gate driver IC in power supply 14.

The FPGA is further used on board to perform fault protection logic using one or more of the fault protection circuits. For instance, the FPGA can detect the over-voltage and the under-voltage. The FPGA may take care of any pulse related faults. The FPGA further functions as a protection signal receiver handling the following tasks: gate driver fault signal receiver; gate driver UVLO signal receiver; 5 V UVLO fault signal receiver; over lapping signal receiver; long time on signal receiver; and HV under voltage fault signal receiver. The FPGA further functions as a protection signal output handling the following tasks: HV converter switch off signal and gate driver off signal.

In embodiments, an EMI (electromagnetic interference filter) is added to power supply 14. The EMI filter may be, for instance, a 'Zorro' filter providing common mode choke and differential mode choke.

In embodiments, an output voltage and current high-speed sensing circuit for measuring purposes is added to power supply 14.

While exemplary embodiments are described above, it is not intended that these embodiments describe all possible forms of the present invention. Rather, the words used in the specification are words of description rather than limitation, and it is understood that various changes may be made without departing from the spirit and scope of the present invention. Additionally, the features of various implementing embodiments may be combined to form further embodiments of the present invention.

What is claimed is:

1. An electromagnetic acoustic transducer (EMAT) system for inspecting a part, comprising:
   an EMAT sensor; and
   a power supply for supplying an output power to the EMAT sensor for the EMAT sensor to use to generate an electromagnetic field, the power supply including a DC/DC converter to boost an input DC voltage into a boosted DC voltage, a DC/AC inverter having Silicon Carbide (SiC) Mosfet power switches to invert the boosted DC voltage into an AC square voltage at a frequency between 50 kHz-2.0 MHz, a DC link capacitor between the DC/DC converter and the DC/AC inverter to be charged with the boosted DC voltage and provide the boosted DC voltage to the DC/AC inverter for the DC/AC inverter to invert the boosted DC voltage into the AC square voltage, and an output filter being a resonant filter consisting of at least an inductor and a capacitor to filter the AC square voltage into an AC sinusoidal voltage at the frequency between 50 kHz-2.0 MHz, wherein the power supply between the DC link capacitor and the output filter is absent of any transformer and the AC sinusoidal voltage is the output power from the power supply to the EMAT sensor.

2. The system of claim 1 wherein:
the power switches of the DC/AC inverter are 1.2-1.7 kV SiC Mosfet power switches capable of switching at a switching frequency up to 2.0 MHz.

3. The system of claim 1 wherein:
the EMAT sensor is an EMAT normal beam sensor; and
the DC/DC converter to boost the input DC voltage into the boosted DC voltage having at least 500 V DC, the DC/AC inverter to invert the boosted DC voltage into the AC square voltage having at least ±600 V AC at a frequency between 1.5-2.0 MHz, and the output filter to filter the AC square voltage into the AC sinusoidal voltage having at least ±600 V AC at the frequency between 1.5-2.0 MHz.

4. The system of claim 1 wherein:
the EMAT sensor is an EMAT guided wave sensor; and
the DC/DC converter to boost the input DC voltage into the boosted DC voltage having at least 500 V DC, the DC/AC inverter to invert the boosted DC voltage into the AC square voltage having at least ±600 V AC at a frequency between 50-200 kHz, and the output filter to filter the AC square voltage into the AC sinusoidal voltage having at least ±600 V AC at the frequency between 50-200 kHz.

5. The system of claim 1 wherein:
the output filter is a LCC filter.

6. The system of claim 1 wherein:
the output filter includes a damping resistor added in parallel to a load of the output filter.

7. The system of claim 1 wherein:
the power supply further includes damping resistors respectively added in series with a DC link of the DC/AC inverter.

8. The system of claim 1 wherein:
the power supply further includes Miller capacitors respectively connected between a drain terminal and a gate terminal of the power switches of the DC/AC inverter.

9. The system of claim 1 wherein:
the power supply further includes a plurality of Zener diodes respectively connected between a gate terminal and a source terminal of the power switches of the DC/AC inverter.

10. The system of claim 1 wherein:
the power supply further includes a plurality of clamping capacitors in parallel with the DC link capacitor.

11. The system of claim 1 wherein:
the DC/AC inverter has a full H-bridge configuration having four power switches.

12. The system of claim 1 wherein:
the DC/DC converter includes a front H-bridge having four Silicon (Si) Mosfet power switches and a rear H-bridge having four Si Mosfet power switches.

13. The system of claim 1 wherein:
the power supply further includes a gate driver IC for each power switch of the DC/AC inverter to amplify gate signals to drive gates of the power switches of the DC/AC inverter, gate resistor circuits respectively for the power switches of the DC/AC inverter and connected to the gate driver IC, and an opto-isolator coupler connected to the gate driver IC.

14. The system of claim 1 further comprising:
a controller to control the power switches of the DC/AC inverter using pulse width modulation (PWM) for the DC/AC inverter to invert the boosted DC voltage into the AC square voltage for when the EMAT sensor is an EMAT normal beam sensor;
the controller to control the power switches of the DC/AC inverter using either PWM or sinusoidal pulse width modulation (SPWM) for the DC/AC inverter to invert the boosted DC voltage into the AC square voltage for when the EMAT sensor is an EMAT guided wave beam sensor; and
wherein the EMAT sensor is one of the EMAT normal beam sensor and the EMAT guided wave sensor.

15. An electromagnetic acoustic transducer (EMAT) system for inspecting a part, comprising:
an EMAT sensor;
a power supply for supplying an output power to the EMAT sensor, the power supply including a DC/DC converter to boost an input DC voltage into a boosted DC voltage, a DC/AC inverter having Silicon Carbide (SiC) Mosfet power switches to invert the boosted DC voltage into an AC square voltage, and an output filter to filter the AC square voltage into an AC sinusoidal voltage, wherein the AC sinusoidal voltage is the output power from the power supply to the EMAT sensor;
the power supply further includes a first filter, a second filter, and a switch operable to implement one of the first filter and the second filter as the output filter of the power supply; and
a controller to control the switch to select the first filter as the output filter of the power supply when the EMAT sensor is an EMAT normal beam sensor and to select the second filter as the output filter of the power supply when the EMAT sensor is an EMAT guided wave sensor.

16. The system of claim 15 wherein:
the first filter is a LCC filter and the second filter is a LCC filter, L and C values of the first filter being different than L and C values of the second filter.

17. The system of claim 15 wherein:
the first filter is a LCC filter and the second filter is a LC filter.

* * * * *